United States Patent [19]

Picone et al.

[11] Patent Number: 5,614,388
[45] Date of Patent: Mar. 25, 1997

[54] PCR PRIMERS FOR DETECTION OF LEGIONELLA SPECIES AND METHODS FOR CONTROLLING VISUAL INTENSITY IN HYBRIDIZATION ASSAYS

[75] Inventors: Teresa K.H. Picone, Benicia; Theresa M. McCallum, Pleasant Hill; Michael A. Zoccoli, Moraga, all of Calif.

[73] Assignee: Hoffmann-La Roche Inc., Nutley, N.J.

[21] Appl. No.: 455,116

[22] Filed: May 31, 1995

Related U.S. Application Data

[63] Continuation of Ser. No. 70,328, filed as PCT/US91/09688, Dec. 19, 1991, Pat. No. 5,491,225, which is a continuation-in-part of Ser. No. 630,899, Dec. 20, 1990, abandoned.

[51] Int. Cl.$^6$ .............................. C12P 19/34; C12N 1/00; C12N 15/00; C07H 21/04
[52] U.S. Cl. ............... 435/91.2; 435/6; 435/91.1; 435/82.2; 436/94; 536/23.1; 536/23.7; 536/24.32; 536/24.33; 536/25.3; 935/77; 935/78
[58] Field of Search ................. 435/6, 91.1, 91.2, 435/822, 183; 436/94; 536/23.1, 23.7, 24.32, 24.33, 25.3; 935/77, 78

[56] References Cited

U.S. PATENT DOCUMENTS

| | | | |
|---|---|---|---|
| 4,683,195 | 7/1987 | Mullis et al. | 435/6 |
| 4,851,330 | 7/1989 | Kohne | 435/6 |
| 5,298,392 | 3/1994 | Atlas et al. | 435/600 |

FOREIGN PATENT DOCUMENTS

| | | | |
|---|---|---|---|
| 438115 | 7/1991 | European Pat. Off. | |
| 88/03957 | 2/1988 | WIPO | C12Q 1/68 |
| 8803957 | 6/1988 | WIPO | |

OTHER PUBLICATIONS

Johnson et al., "Bergy's Manual of Systematic Bacteriology" vol. 1 published 1984 by Williams and Wilkins (Baltimore) pp. 88–11.
Grimont et al., 1985, "DNA Probe Specific for Legionella pneumophila" J. Clin. Microbiol. 21(3):431–437.
Chumakov et al., 1986, "Use of 5S Ribosomal RNA Nucleotide Sequence Analysis for the Study of Phylogeny of the Genus Legionella" Mol. Genet. Mikrobiol. Birusol. 8:38–40.
Engleberg et al., 1986, "A Legionella–Specific DNA Probe Detects Organisms in Lung Tissue Hormogenates From Intranasally Inoculated Mice" Israel J. of Med. Sciences 22:703–705.
Hussong et al., 1987, "Viable Legionella Pneumophila Not Detectable by Culture on Agar Media" Bio/Technology 5:947–950.
MacDonell et al., 1987, "The Nucleotide Sequence of the 5S rRNA From Legionella pneumophila" Nucleic Acids Research 15(3)1335.

Muraca et al., 1988, "Environmental Aspects of Legionnaires' Disease" J. Amer. Water Works Assoc. 80:78–86.
Steffan et al., 1988, "DNA Amplification to Enhance Detection of Genetically Engineered Bacteria in Environmental Samples" Appl. Environ. Microbiol. 54(9):2185–2191.
Bottger et al., 1989, "Rapid Determination of Bacterial Ribosomal RNA Sequences by Direct Sequencing of Enzymatically Amplified DNA" FEMS Microbiology Letters 65:171–176.
Cianciotto et al., 1989, "A Legionella pneumophila Gene Encoding a Species–Specific Surface Protein Potentiates Initation of Intracellular Infection" Infection and Immunity 57:1255–1262.
Clesceri et al., "Legionellaceae" Standard Methods for the Examination of Water and Wastewater 17th Ed. Chapter 9260 J. pp. 9–149 through 9–153 (1989).
Engleberg et al., 1989, "DNA Sequence of mip, a Legionella pneumophila Gene Associated With Macrophage Infectivity" Infection and Immunity 57(4):1263–1270.
Starnbach et al., 1989, "Species–Specific Detection of Legionella pneumophila in Water by DNA Amplification and Hybrization" J. Clin. Microbiol. 27(6):1257–1261.
"Detection of Legionella in Environmental Samples Using Polymerase Chain Reaction (PCR)" Biotechnology Bulletin pp. 11–12 (May, 1990).
Cianciotta et al., 1990, "A Mutation in the mip Gene Results in an Attenuation of Legionella pneumophila Virulence" J. Infect. Diseases 161:121–126.
Cianciotto et al., 1990, "Identification of mip–Like Genes in the Genus Legionella" Infection and Immunity 58(9):2912–2918.
Alder et al., 1989, "Nucleic Acid Amplification and Hybridization Method for Rapid Nucleic Acid Detection" Chemical Abstracts 112(25):232270X (Accession No. CA112).
Picone et al., 1991, "Multiplex–PCR Based Assay for the Genus Legionella and Species L. Pneumophila" Abstr. Gen. Am. Soc. Microbiol. 91:300 (abstract No. Q–145).

*Primary Examiner*—Bradley L. Sisson
*Attorney, Agent, or Firm*—George W. Johnston; Stacey R. Sias; Douglas A. Petry

[57] ABSTRACT

This invention provides for superior nucleic acid primers for amplification of select target regions of the genome of the genus Legionella. The invention facilitates detection of pathogenic and nonpathogenic forms of this genus. The invention further provides for processes for using the primers in template dependent nucleic acid polymerase extension reactions to amplify select target regions. Kits for the use of these primers are also provided.

This invention further provides for methods of controlling the intensity of visual signal for detection of duplex formation in nucleic acid hybridization assays under high stringent conditions. This method involves the blending of different capture probes onto a solid support.

6 Claims, No Drawings

PCR PRIMERS FOR DETECTION OF LEGIONELLA SPECIES AND METHODS FOR CONTROLLING VISUAL INTENSITY IN HYBRIDIZATION ASSAYS

This application is a continuation of application Ser. No. 08/070,328, filed May 27, 1993, U.S. Pat. No. 5,491,225, which is a 371 of PCT/US91/09688, Dec. 19, 1991, and a Continuation-in-part of Ser. No. 07/630,899, filed Dec. 20, 1990, abandoned.

BACKGROUND OF THE INVENTION

1. Field of the Invention

This invention provides for superior nucleic acid primers for amplification of select target regions of the genome of the genus Legionella. The invention facilitates detection of pathogenic and nonpathogenic forms of this genus. The invention further provides for processes for using the primers in template dependent nucleic acid polymerase extension reactions to amplify select target regions. Kits for the use of these primers are also provided.

This invention further provides for methods of controlling the intensity of visual signal for detection of duplex formation in nucleic acid hybridization assays under high stringent conditions. This method involves the blending of different capture probes onto a solid support.

2. Information Disclosure

Legionella species are known as both pathogenic and nonpathogenic microorganisms. In the pneumonic form, they are intracellular pathogens of lung macrophage cells. Legionellaceae, Chpt. 9260 J. in Standard Methods of the Examination of Water and Wastewater, Eds. Clesceri, Greenberg and Trussell, 17th Ed. 1989 pages 9-149 to 9-153 and Muraca, P. W. et al., 1988, Environmental Aspects of Legionnaires' Disease, *J. Amer. Water Works Assoc.* 80:78–86.

A surface antigen of Legionella has been implicated as a requirement for intracellular pathogenicity and is called a macrophage infectivity potentiator or mip. Cianciotto, N. P. et al., 1989, A *Legionella pneumophila* Gene Encoding a Species-specific Surface Protein Potentiates Initiation of Intracellular Infection, *Infection and Immunity*, 57:1255–1262.

The nucleotide sequence of the 5S rRNA has been reported by MacDonnell, M. T. and R. R. Colwell, 1987, The Nucleotide Sequence of the 5S rRNA From *Legionella pneumophila, Nucleic Acid Research*, 15:1335; and, by Chumakov, K. M et al., 1986, Use of 5S Ribosomal RNA Nucleotide Sequence Analysis for the Study of Phylogeny of the Genus Legionella, *Mol. Genet., Mikrobiol Virusol.*, 8:38–40.

The nucleotide and amino acid sequence of the macrophage infectivity protein is known and reported by Engleberg, N. C. et al., 1989, DNA Sequence of mip, a *Legionella pneumophila* Gene Associated With Macrophage Infectivity, *Infection and Immunity*, 57:1263–1270.

Standard culture techniques for Legionella are not adequate to properly assess risks from this deadly patbogen. Hussong, D. et al, 1987, Viable *Legionella pneumophila* Not Detectable by Culture on Agar Media, *Bio/Technology* 5:947–950.

Nucleic acid probes for detection of *Legionella pneumophila* have been reported. Grimont, P. A. D. et al., 1985, DNA Probe Specific for *Legionella pneumophila, J. Clin. Micro.*, 21:431–437; and Engleberg, N. C. et al., 1986, A Legionella-Specific DNA Probe Detects Organisms in Lung Tissue Homogenates from Intranasally Inoculated Mice, *Israel J. of Med. Sciences*, 22:703–705.

The use of polymerase chain reaction amplification methods to detect Legionella species has been disclosed by Starnbach, M. N. et al., 1989, Species-Specific Detection of *Legionella pneumophila* in Water by DNA Amplification and Hybridization, *J. of Clin. Microbiol.*, 27:1257–1261; in U.S. Ser. No. 07/467,813 filed on Jan. 1, 1990; and, also in Detection of Legionella in Environmental Samples Using Polymerase Chain Reaction (PCR), *Biotechnology Bulletin*, May 1990 pages 11–12.

SUMMARY OF THE INVENTION

This invention provides for superior amplification primers for use in assays for detecting pathogenic Legionella species. Described primers are able to amplify select regions of the 5 S RNA gene that are uniquely common to most species of Legionella. Other primers are able to discriminate between Legionella having the mip gene and those without the mip gene. The primers are further advantageous in that they have similar thermal melting points and can be used in combination to efficiently and equally amplify more than one region of the Legionella genome in a single amplification reaction mixture.

In particular, this invention provides for a composition comprising multiple pairs of amplification primers for amplifying subsequences of the 5 S RNA gene and mip gene of Legionella species each primer having a thermal melting point with respect to their binding sites of less than about 8° C. of each other. Methods for amplifying genomic regions of Legionella using these compositions are also described herein.

This invention further provides for nucleic acid polymerase primers for the amplification of subsequences of nucleic acid from Legionella species wherein the primers bind substantially to the nucleic acid subsequence selected from the group consisting of (a) 3'-CGTAACCACG-GCTAAACC-5'; Seq. ID No. 12; (b) 3'-CGAAACGG-TAGTTTAGAAAGACTT-5'; Seq. ID No. 13; (c) 3'-CCGCTGATATCGCYAAACCTT-5'; Seq. ID No. 14; (d) 3'-CGCTACTGGATGAAAGYGTACT-5'; Seq. ID No. 15; (e) 3'-CCGCTGATATCGCCACACCTT-5'; Seq. ID No. 18; (f) 3'-CGCTACTGGATGAAAGCGTAC-5'; Seq. ID No. 19; and (g) 3'-CAAAACGGTAGTTTAGAAAAACTT-5'; Seq. ID No. 20 where Y represents a cytosine or thymine base and the primers having a base Y encompass a mixture of the two primers. Examples of such primers are: (a) 5'-GCATTGGTGCCGATTTGG-3'; Seq. ID No. 6; (b) 5'-GCTTTGCCATCAAATCTTTCTGAA-3'; Seq. ID No. 7; (c) 5'-GGCGACTATAGCGRTTTGGAA-3'; Seq. ID No. 10; (d) 5'-GCGATGACCTACTTTCRCATGA-3'; Seq. ID No. 9; (e) 5'-GGCGACTATAGCGGTGTGGAA-3'; Seq. ID No. 21; (f) 5'-GCGATGACCTACTTTCGCATG-3'; Seq. ID No. 22; and (g) 5'-GTTTTGCCATCAAATCTTTTTGAA-3'; Seq. ID No. 23 where R represents an adenine or a guanine base and the primers having a base R are a mixture of the two primers.

This invention also provides for an internal positive control oligonucleotide sequence comprising an unnatural oligonucleotide subsequence flanked by primer binding sites. In this fashion the IPC will amplify with the same primer pairs used to amplify the target subsequence. In one embodiment of the present invention, the target is the mip gene of Legionella species. In this embodiment the IPC comprises an unnatural subsequence flanked by the following nucleic acid subsequences: (a) 3'-CGTAACCACGGCTAAACC-5'; Seq. ID No. 12; and, (b) 3'-CGAAACGGTAGTTTAGAAAGACTT-5'; Seq. ID No. 13. In another embodiment the primer binding sites of the IPC will be identical to the primer binding sites of the 5 S RNA gene target. In this embodiment the primer binding sites will comprise (c) 3'-CCGCTGATATCGCYAAACCTT-5'; Seq. ID No. 14; and/or, (d) 3'-CGCTACTGGATGAAAGYGTACT-5'; Seq. ID No. 15; and/or, (e) 3'-CCGCTGATATCGCCACACCTT-5'; Seq. ID No. 18; and/or, (f) 3'-CGCTACTGGATGAAAGCGTAC-5'; Seq. ID No. 19 where Y represents a cytosine or thymine base. More specifically there is disclosed an IPC oligonucleotide sequence having either one or both of the following sequences 5'-GCATTGGTGCCGATTTGG-3'; Seq. ID No. 6 and 5'-TTCAGAAAGATTTGATGGCAAAGC-3'; Seq. ID No. 13.

It should be understood that alternative primers could be envisioned deviating from those described. Deviations might include minor base changes, biotinylated bases, base analogs or additional bases added to the primer ends. Wherever such modifications or changes do not substantially affect the primers' ability to amplify the target region internal to the stated binding sites for the named primers such modified primers are considered to be within the scope of this invention.

This invention further embraces processes utilizing the above amplification primers. Preferably in a multiplex PCR format. In particular there is disclosed a process of using nucleotide polymerases for amplification of nucleic acid subsequences from Legionella species wherein the polymerases initiate subsequence amplification by extension of nucleic acid primers which bind substantially to a nucleic acid subsequence selected from the group consisting of: (a) 3'-CGTAACCACGGCTAAACC-5'; Seq. ID No. 12; (b) 3'-CGAAACGGTAGTTTAGAAAGACTT-5'; Seq. ID No. 13; (c) 3'-CCGCTGATATCGCYAAACCTT-5'; Seq. ID No. 14; (d) 3'-CGCTACTGGATGAAAGYGTACT-5'; Seq. ID No. 15; (e) 3'-CCGCTGATATCGCCACACCTT-5'; Seq. ID No. 18; (f) 3'-CGCTACTGGATGAAAGCGTAC-5'; Seq. ID No. 19; and (g) 3'-CAAAACGGTAGTTTAGAAAAACTT-5'; Seq. ID No. 20 where Y represents a cytosine or thymine base and the primers having a base Y are a mixture of the two primers. This invention also provides for the above process where the primers are as described above and where an internal positive control oligonucleotide sequence is included in the amplification mixture.

This invention provides for kits for the amplification of nucleic acid from Legionella species comprising a compartment which contains a nucleic acid which binds substantially to a nucleic acid subsequence as described above and preferably containing the primers as described above. Internal positive control oligonucleotide sequence are also included in an alternative embodiment of these kits.

A second aspect of the disclosed invention relates to controlling the intensity of the visual signal used to detect duplex formation in nucleic acid hybridization assays. The model is a nucleic acid hybridization assay kit for the detection of a particular genus having numerous distinct species. In some cases detection and discrimination of a particular species may be desirable especially where a particular species is known to be of medical importance. In other cases where most of the species of organisms within a genus have been associated with disease, it is desirable to detect the presence the entire genus of organisms. It is further desirable that the detection of the genus of organisms be obtained as one positive visual response regardless of species. If the target nucleic acid sequence used for the detection of the genus of organisms varies for different species within the genus it is typically necessary to lower the stringency of hybridization or utilize multiple capture probes. This invention avoids this problem of resorting to low stringent conditions.

Lower stringent conditions are routinely used to accommodate the capture of multiple target sequences that contain variations in their nucleic acid sequences. The stringency is reduced by either lowering the temperature of hybridization and wash or by modification of the buffer. When the stringent conditions are reduced and the target nucleic acid sequence is very similar to nucleic acid sequences of another genus of organisms specificity of the capture probe for the target genus can be lost.

When multiple capture probes are used and are selected to be compatible to variations in the target nucleic acid sequences, the specificity under high stringent conditions can be regained. The blending of multiple probes permits a single positive response for the presence of a group of target organisms. Without this invention, the different capture probes would normally be immobilized individually on a solid support. As a result, the assay would require the use of more test sample, more time to perform the test and more interpretation by the user.

In those kits utilizing this invention, the multiple capture probes are blended together and immobilized in such a manner to accommodate the detection of the various species of the genus of organisms in a single test. The probes are selected to be compatible to blending (i.e. contain non-complementary sequence and have as similar as possible melting temperatures). The capture probes should be blended in the proper ratio to generate a result of equal intensity for species within the genus of organisms to minimize interpretation of the result when semiquantitation and equal sensitivity for all target organisms are desirable. Depending on the hybridization characteristics, the concentration each capture probe in the blended may or may not be equal. It is possible to determine the proper capture probe blend by a series of titrations. The blends of the capture probes of varying ratios are created and immobilized on a solid support.

The capture probes are individually immobilized on the solid support for reference in the titration of the probe blend. Nucleic acid from different species within the genus of organisms to be tested are hybridized to the capture probe blends and to the individual probes. The probe blend that generates the same response as an individual specific probe for the species within the genus is chosen for use as a capture probe blend in the kit. These capture probes may also be individually be immobilized as capture probes should further speciation be desired but it is not necessary.

It should be noted that the mixture of capture probes may or may not contain all probes for the same gene provided that they have similar hybridization characteristics.

The mixture of capture probes may be able to capture more than one genus if desired. For example, should a kit be developed that detects food borne pathologies such as the genus Salmonella and Shigella, a mixture of probes can be used to indicate a pathogen is present of either of the two genera. This may be all that is necessary for the food laboratory. If further identification is necessary (maybe for food poisoning problem) then the same capture probes may be used for identification in separate and uriblended states.

More specifically, this invention provides for a method for controlling visual density of detection probes bound to capture probes in a nucleic acid hybridization assay having a first and a second capture probe wherein the nucleic acid sequences of the two capture probes are different, said method comprising: (a) mixing a blend of the two different capture probes; (b) affixing the mixture of probes from step (a) and the first capture probe to discrete first and second regions of a solid support wherein the concentration of the first capture probe is equal in both regions; (c) binding the detection probes to the capture probes of step (b) under high stringent hybridization conditions such that the detection probes bind to one capture probe but not the other; and (d) detecting hybridization of the detection probe by visual density; wherein the proportion of the two capture probes in the blend of step (a) is adjusted to give a visual density in the first region equal to that of the second region having the first capture probe when equal amounts of the detection probes are present in a test sample. The concentration of the second probe in the second region will not be the same as the concentration of the second probe in the first region. Typically the second probe is not present in the second region.

The detection probe can be an amplification product such as a PCR amplification product. The assay format can involve a detection probe which is a complex of a target nucleic acid which binds under high stringent hybridization conditions to different regions of the capture and signal probe and wherein the capture and signal probes do not hybridize to each other.

Furthermore it is preferred that this method deliberately provide for a proportion of the two capture probes adjusted according to a known quantity of target nucleic acid. The detection range for the assay is in a concentration range of between about $10 \times 10^{-12}$ to about $100 \times 10^{-9}$ molar. It being desired that the assay provide, a positive gradient of visual density over a target nucleic acid concentration of between about $10 \times 10^{-12}$ to about $100 \times 10^{-9}$ molar.

Kits embracing the above method are also a part of this invention. In particular there is contemplated a nucleic acid hybridization kit providing equal visual density for positive results in a test sample. The kit uses detection probes and a first and a second capture probe wherein the capture probes have different nucleic acid sequences, said kit comprising the following components: (a) a solid support having a first discrete region having a concentration of the first and second capture probes affixed thereto; (b) a solid support having a second discrete region wherein the first capture probes are affixed thereto in a concentration equal to the concentration of the first probe in the mixture described in component (a); and, (c) a container containing detection probes; wherein the proportion of the two capture probes in the mixture of component (a) is adjusted to give a visual density equal to that of the solid support of component (b) under identical hybridization conditions and with equal amounts of the detection probes present in the test sample. The concentration of second probe in the second region is not the same as its concentration in the first region and is typically not present.

DEFINITIONS

"Affixing" in the context of nucleic acids and solid supports refers to the binding or attaching of the nucleic acids to solid supports by conventional means such as covalent or electrostatic bonding.

"Amplification reaction mixture" refers to an aqueous solution comprising the various reagents used to amplify a target nucleic acid. These include enzymes, aqueous buffers, salts, target nucleic acid, and nucleoside triphosphates. Depending upon the context, the mixture can be either a complete or incomplete amplification reaction mixture.

"Amplification reaction system" refers to any in vitro means for multiplying the copies of a target sequence of nucleic acid. Such methods include but are not limited to PCR, DNA ligase, QB RNA replicase and RNA transcription-based amplification systems. These involve multiple amplification reagents and are more fully described below.

"Amplification reaction tube(s)" refers to container suitable for holding the amplification reagents. Generally the tube is constructed of inert components so as to not inhibit or interfere with the amplification system being used. Where the system requires thermal cycling of repeated heating and cooling, the tube must be able to withstand the cycling process and typically precisely fit the wells of the thermocycler.

"Amplification reagents" refer to the various buffers, enzymes, primers, nucleoside triphosphates both conventional and unconventional, and probes used to perform the selected amplification procedure.

"Amplifying" or "Amplification" which typically refers to an "exponential" increase in target nucleic acid is being used herein to describe both linear and exponential increases in the numbers of a select target sequence of nucleic acid.

"Bind(s) substantially" refers to complementary hybridization between oligonucleotides and embraces minor mismatches which can be accommodated by reducing the stringency of the hybridization media to achieve the desire priming of the PCR polymerases.

"Biotinylated" refers to a biotin moiety covalently attached to the 5' end of an oligonucleotide for the purpose of reacting with streptavidin in a detection assay.

"Bound" in the context of nucleic acids refers to the hybridization of the nucleic acids through complementary base pairing.

"Capture probes" refer to oligonucleotides which are bound to a solid support and are capable of hybridizing with detection probes either directly or indirectly through target nucleic acid. The capture probes may be bound to the solid support through a variety of known means including covalent bonds and electrostatic bonds.

"Concentration" refers to the molar amount of a substance in a given amount of volume or space.

"Detection probes" refers to nucleic acids which bind to capture probes. The detection probe either is directly detectable as with a radioisotope incorporated into the sequence or indirectly labelled as with biotin wherein a streptavidin/enzyme complex is subsequently bound. Detection probe is also meant to include a target nucleic acid/signal probe complex of a ternary or quaternary sandwich hybridization assay. Such systems typically require the target nucleic acid to bind to the capture probe and the signal probe then binds to the target nucleic acid.

"Discrete" refers to regions of capture nucleic acid affixed to the solid support having boundaries which provide separation and identification allowing one to distinguish between other regions of capture nucleic acid.

"High stringent hybridization conditions" refers to temperature, solute concentrations and polarity of a given hybridization medium which provides detectable differences in hybridization rates between oligonucleotides of between 10 and 30 bases wherein the oligonucleotides mismatch their respective complementary bases by 1 mismatched base pair.

The different hybridization rates are distinguished using the detection system of the given assay.

"Internal positive control (IPC) oligonucleotide sequence" refers to a recombinant or synthetic oligonucleotide that amplifies with the same primer pair used to amplify target nucleic acid. IPC oligonucleotide sequences are used to ensure assay users that the amplification process has occurred in the event that the sample being tested has no target nucleic acid. These oligonucleotides are flanked at one or both ends by a sequence complementary to the binding site of an amplification primer used in the amplification process. The internal target subsequence is a foreign sequence not naturally found adjacent to the binding sites of the amplification primers. The internal control oligonucleotide sequences thus serve as templates for the amplification primers to establish that the amplification reaction would have amplified target nucleic acid if such target had been present. IPC oligonucleotide sequences can be supplied as single or double stranded nucleotides. When single stranded those of skill would recognize that to facilitate non-linear amplification the 5' end of the IPC should have base identity with the other primer of the pair.

"Legionella species" include those members of the family Legionellaceae. It is one genus family composed of more than 22 species. It should be recognized that the taxonomy of prokaryotes is not static and that additional species might be named or that these species may some day be incorporated into an alternative family or genus.

"Nucleic acid" refers to a deoxyribonucleotide or ribonucleotide polymer in either single or double stranded form and unless otherwise limited would encompass known analog of natural nucleotides which can function in a similar manner as naturally occurring nucleotides.

"Nucleotide polymerases" refers to enzymes able to catalyze the synthesis of DNA or RNA from nucleoside triphosphate precursors. In the amplification reactions of this invention the polymerases are template dependent and typically extend from the 3' end of the polymer being formed. It is most preferred that the polymerase is thermostable as described in U.S. Pat. No. 4,889,819 and U.S. Ser. No. 7/143,141, filed Jan. 12, 1988, now abandoned.

"Positive gradient of visual density" refers to a response of visual density which increases with the presence of an increased presence of detection probe. In the assays described herein it is possible to provide a dynamic range of concentrations wherein an increase in detection probe is noticeable. Below this range, there is little or no visible density and above the range, increased detection probe in a sample will not yield increased visual density.

"Primer" or "nucleic acid polymerase primer(s)" refers to an oligonucleotide, whether natural or synthetic, capable of acting as a point of initiation of DNA synthesis under conditions in which synthesis of a primer extension product complementary to a nucleic acid strand is initiated, i.e., in the presence of four different nucleotide triphosphates and an agent for polymerization (i.e., DNA polymerase or reverse transcriptase) in an appropriate buffer and at a suitable temperature. A primer is preferably an oligodeoxyribonucleotide and is single stranded for maximum efficiency in amplification, but may also be double stranded. If double stranded, the primer is first treated to separate its strands before being used to prepare extension products. The exact length of a primer will depend on many factors, but typically ranges from 15 to 25 nucleotides. Short primer molecules generally require cooler temperatures to form sufficiently stable hybrid complexes with the template. A primer need not reflect the exact sequence of the template but must be sufficiently complementary to hybridize with a template. An example of a non-complementary sequence which may be incorporated into the primer is a sequence which encodes a restriction enzyme recognition site (see U.S. Pat. No. 4,800,159).

A primer can be labeled, if desired, by incorporating a label detectable by spectroscopic, photochemical, biochemical, immunochemical, or chemical means. For example, useful labels include $^{32}P$, fluorescent dyes, electron-dense reagents, enzymes (as commonly used in ELISAS), biotin, or haptens or proteins for which antisera or monoclonal antibodies are available. A label can also be used to "capture" the primer, so as to facilitate the immobilization of either the primer or amplified DNA on a solid support.

"Proportion of the two capture probes in the blend" refers to the relative concentrations of the probes,(i.e., 1:1 or 2:1).

"Signal probe" refers to an oligonucleotide which comprises a detectable label. This term is generally used to differentiated between the target nucleic acid and capture probe in a ternary or quaternary sandwich assay format. The label can be any of the reporter or signal systems described for the detection probe.

"Solid support" refers to any insoluble material which can provide a substrate upon which to affix capture nucleic acids. Such substrates may include nylon, amino or carboxy activated plastics, glass, cellulose and the like.

"Subsequence" refers to a sequence of nucleic acids which comprises a part of a longer sequence of nucleic acids.

"Target region" refers to a region of a nucleic acid which is to be analyzed, which usually contains polymorphic DNA sequences.

"Target nucleic acid" refers to a nucleic acid which complexes with a signal probe to provide the detection probe. Such nucleic acids are typically used in the sandwich assay formats wherein the target nucleic acid binds to a capture probe and the signal probe binds to the target nucleic acid.

"Test Sample" refers to an aqueous hybridization medium containing detection probes.

"Uniform density" refers to equivalent density either through visual recording with the eye or with an analytic instrument such as a densitometer or colorimeter.

"Visual density" refers to the relative intensity of the signal or detection product produced by the labelling system used to measure the presence or absence of duplex. formation between complementary oligonucleotides. The choice of labelling systems is not critical. The system can be direct or indirect and may be radioactive, fluorescent, luminescent or colorimetric. Density may be determined either by photographic means, analytic instruments or by the naked eye. Enzymatic colorimetric labeling systems are preferred.

DETAILED DESCRIPTION

Introduction:

The detection of Legionella species using PCR to amplify nucleic acid from these species requires multiple steps. These steps include an adequate sampling procedure to isolate and/or concentrate the extant organisms to a suitable degree for detection, a method for lysing the cells to release nucleic acid, a suitable procedure to amplify the target nucleic acid sequences and a means to detect the amplified sequences. A general description of this methodology can be found in Atlas, R. M. and Bej, A. K., Detecting Bacterial Pathogens in Environmental Water Samples by Using PCR and Gene Probes in *PCR Protocols,* Ed. Innis et al., Academic Press, Inc. 1990 at pages 399–406.

To effectively amplify target nucleic acid subsequences, PCR requires primers to initiate polymerase extension. The selection of primers is an important aspect of this invention and the particular primers disclosed herein solve various problems associated with other primers purported to function adequately for the detection of Legionella species. Such problems relate to the binding of primers to hairpin turns within the genome, undue internal secondary structure within primers themselves, non-specific binding of the primers to both target regions and to non-target regions, unequal thermal melting points such that the primers are not all efficiently binding at the same temperature and maintaining relatively short amplified product.

The 5S RNA gene amplification primers of this invention are able to amplify numerous species of the Legionella genus (see Table 1). They advantageously do not amplify closely related species from the genus Pseudomonas or Flavobacterium. The mip primers are specific for their ability to amplify the mip gene of *L. pneumophila, L. hackeliae* and strains of *L. sainthelensi*.

Sampling systems:

Legionella exists in warm aquatic environments. Human infections of pathogenic Legionella often involve aerosol exposure to warm fresh water such as that found in air conditioning systems and residential water supplies. For purposes of sampling, suspect water is collected and either subjected to low speed centrifugation (eg., 10,000×g for 15 minutes) or filtered to concentrate or collect the Legionella. Legionella are trapped by filters having a porosity of about 0.45 μm. A prefilteration step can be useful where physical debris may interfere with the subsequent filtration or amplification procedures. The prefilter is a noncritical feature of this invention. Such filters are generally of a porosity and composition that will allow the Legionella bacterium to pass freely through it. The physical means for water collection are well known and include sterile glass vials, syringe assemblies and other inert vessels suitable for storage of water.

Sample preparation:

Relatively clean water samples may be directly assayed without isolation or purification of the target nucleic acid prior to amplification. Large water samples may be filtered to concentrate microbial populations. Filtering procedures and filters are well-known to those of skill. See, for example, *Standard Method For The Examination Of Water and Wastewater*, 17th Ed., page 9–14, published by the Amer. Publ. Health Assoc., 1015 Fifteenth St. N.W., Washington, D.C. 20005. Preferred filters have a porosity which will trap Legionella cells yet permit extraneous nucleic acid to pass. Teflon membranes such as Fluoropore FGLP 0013 of 0.2 μM, or 0.5 μM pore size (Millipore Corp., Bedford, Md.), or Duropore HVLP are of use in this invention.

The water samples or filter concentrated samples are subjected to conditions sufficient to release the target nucleic acid from the suspect organisms. Mechanical lysis is preferred. Mechanical lysis can be achieved by sonication, boiling or multiple freeze/thaw cycles. Boiling the sample in the presence of Chelex®, resin is preferred. Chemical means of cell disruption are also operable and include standard lysing means such as lysozymes, osmotic shock, protease K treatment, and detergents. Chemical methods are less preferred because of possible detrimental effects on the PCR process, (ie. inhibition of the Taq polymerase).

The samples can be heated to denature proteases and nucleases which might interfere with the components of the PCR reaction mixture. Heating the samples to 85° C. for about 5 minutes is generally sufficient. Alternatively, chemical nuclease and protease inhibitors can be used.

When the sample is a complex mixture such as from a patient suspected of being infected with Legionella, it may be preferable to isolate the nucleic acid from the original sample. A variety of techniques for extracting nucleic acids from biological samples are known in the art. For example, see those described in Higuchi, "Simple and Rapid Preparation of Samples for PCR" chapter 4 in *PCR Technology* ed. Erlich, Stockton Press 1989); Maniatis et al., 1989, *Molecular Cloning: A Laboratory Manual,* (New York, Cold Spring Harbor Laboratory, 1982; Hagelberg and Sykes, 1989, *Nature* 342:485; or Arrand, Preparation of Nucleic Acid Probes in Nucleic Acid Hybridization, *A Practical Approach,* Ed Hames and Higgins, IRL Press. pp. 18–30, 1985. Whole nucleic acid extraction procedures typically involve an initial contacting with phenol, phenol/chloroform or guanidinium salts, followed by an alcohol precipitation. Genomic DNA may be obtained from a whole nucleic acid extraction by using Rnase before further alcohol precipitation.

PCR procedures:

Although the PCR process is well known in the art (see U.S. Pat. Nos. 4,683,195 and 4,683,202 which are incorporated herein by reference) and although a variety of commercial vendors, such as Perkin-Elmer or Perkin-Elmer Cetus instruments, sell PCR reagents and publish PCR protocols, some general PCR information is provided below for purposes of clarity and full understanding of the invention to those unfamiliar with the PCR process.

To begin the PCR process, the target nucleic acid in the sample is denatured (assuming the sample nucleic acid is double-stranded). Denaturation is typically achieved by heating the samples. This is because chemical denaturants may inhibit the polymerase activity.

Once the strands are separated, the next step in PCR involves hybridizing the separated strands with primers that flank the target region or subsequence. The primers are then extended to form complementary copies of the target strands, and the cycle of denaturation, hybridization, and extension is repeated as many times as necessary to obtain the desired amount of amplified nucleic acid.

Template-dependent extension of primers in PCR is catalyzed by a polymerizing agent in the presence of adequate amounts of four deoxyribonucleotide triphosphates (dATP, dGTP, dCTP, and dTTP) in a reaction medium comprised of the appropriate salts, metal cations, and pH buffering system. Suitable polymerizing agents are enzymes known to catalyze template-dependent DNA synthesis. For example, if the template is RNA, a suitable polymerizing agent to convert the RNA into a complementary DNA (CDNA) sequence is reverse transcriptase (RT), such as avian myeloblastosis virus RT. Once the target for amplification is DNA, suitable polymerases include, for example, *E. coli* DNA polymerase I or its Klenow fragment, $T_4$ DNA polymerase, and Taq polymerase, a heat stable DNA polymerase isolated from *Thermus aquaticus* and commercially available from PECI. The latter enzyme, Taq DNA polymerase, is widely used in the amplification and sequencing of nucleic acids. The reaction conditions for using DNA polymerases are known in the art, and are described in, for example, the treatise *Methods in Enzymology,* and in Maniatis et al., *Molecular Cloning: A Laboratory Manual,* supra.

During the PCR process, the temperature is very carefully controlled so that strand separation and primer annealing and extension occur in equilibrium. The control of temperature is typically achieved using dry heat generated from a thermocycler.

In the preferred embodiment of the PCR process, the reaction is catalyzed by a thermostable DNA polymerase enzyme, such as Taq DNA polymerase, and carried out at an elevated temperature. The preferred temperature is one at which the enzyme is thermostable, and at which the nucleic acids are in an equilibrium of single and double strands, so that sufficient primer will anneal to template strands to allow a reasonable rate of polymerization. Strand separation is achieved by heating the reaction to a sufficiently high temperature for sufficient time to cause the denaturation of the duplex, but not to cause an irreversible denaturation of the polymerase.

The PCR method can be performed in a step-wise fashion, where after each step new reagents are added, or in a fashion where all of the reagents are added after a given number of steps. For example, if strand separation is induced by heat, and the polymerase is heat-sensitive, then the polymerase will have to be added after every round of strand separation. However, if, for example, a helicase is used for denaturation, or if a thermostable polymerase is used for extension, then all of the reagents may be added initially, or, alternatively, if molar ratios of reagents are of consequence to the reaction, the reagents may be replenished periodically as they are depleted by the synthetic reaction.

Those skilled in the art will know that the PCR process is most usually carried out as an automated process with a thermostable enzyme. In this process, the reaction mixture is cycled through a denaturing step, a primer annealing step, and a extension step. A DNA thermocycler, a machine specifically adapted for use with a thermostable enzyme is disclosed more completely in EP 236,069 and U.S. Pat. No. 4,889,819. DNA Thermocyclers are commercially available from Perkin-Elmer or Perkin Elmer Cetus Instruments (PECI), Norwalk, Conn.

A preferred mode for carrying out the PCR reaction is the multiplex mode. The multiplex mode involves the simultaneous amplification of different target regions using more than one set of PCR primer pairs. The multiplex procedure is preferably designed around primer pairs which have similar thermal melting points. It is preferred that all pairs have Tms within 8° of each other and that the average Tm is between 45° and about 70° C. with preference for an average Tm of between 60° and 70° C.

Selection of the Legionella specific primers:

The primers of this invention are provided in Table 2. The primer pairs responsible for amplifying the 5S rRNA of Legionella species are a degenerate mixture of primers. This mixture is valuable for ensuring that only target DNA from Legionella 5S RNA is amplified. By comparison and empirical analysis it was determined that the left and right primers for the 5S RNA will encompass at least five species of Legionella including the important pathogenic forms. These include *L. pneumophila*, isolates Bloomington, Knoxville-1, Philadelphia-1 and Togus-1), *L. pneumophila* fraseri (Los Angeles), *L. bozemanii* and *L. dumoffii*, *L. jordanis*, *L. gormanii*, *L. longbeachae* and will not react to the DNA of common bacteria present in water samples, ie., *Flavobacterium rigense*, *Pseudomonas fluorescens* and *aerogenes*, *Proteus vulgaris*, and *Escherichia coli*. Table 1 provides a list of Legionella species able to be detected using the disclosed 5S RNA primers. These primers also have compatible Tms of about 65° C. and bind to regions of target sequences having relatively low secondary structure.

The left and right primers for the mip gene are directed to amplify that region of the gene which is specific for pathogenicity and able to identify the species *L. pneumophila* from most other Legionella species. Both these primers have Tms of about 68° C. and bind to highly conserved regions of the Legionella genome that have little tendency to form secondary structures such as hairpins,

TABLE 1

Legionella species having target 5 S RNA genes amplified by PT82 and PT80

1. *Legionella pneumophilia* SG4
2. *L. pneumophilia* SG3
3. *L. pneumophila* SG11
4. *L. pneumophila* SG6
5. *L. pneumophila* SG7
6. *L. pneumophila* SG10
7. *L. longbeachae* SG1

TABLE 1-continued

Legionella species having target 5 S RNA genes amplified by PT82 and PT80

8. *L. pneumophila* SG2
9. *L. hackeliae* SG1
10. *L. pneumphilia* SG1
11. *L. feeleii* SG2
12. *L. pneumophila* SG9
13. *L. erythra*
14. *L. jordanis*
15. *L. pneumophila* SG15
16. *L. tucsonensis*
17. *L. pneumophila* SG12
18. *L. dumoffii*
19. *L. pneumophila* SG8
20. *L. jamestowniensis*
21. *L. spiritensis*
22. *L. sainthelensi* SG1
23. *L. maceachernii*
24. *L. moravica*
25. *L. quinlivanii*
26. *L. cincinnatienisis*
27. *L. bozemanii* SG1
28. *L. parisiensis*
29. *L. feeleii* SG1
30. *L. parisiensis*
31. *L. feeleii* SG1
32. *L. santicrucis*
33. *L. pneumophila* SG5
34. *L. birminghamensis*
35. *L. cherrii*
36. *L. bozmannii* SG2
37. *L. micdadei*
38. *L. oakridgensis*
39. *L. gratiana*
40. *L. pneumophila* SG14
41. *L. anisa*
42. *L. pneumophila* SG13
43. *L. gormanii*
44. *L. wadsorthii*
45. *L. longbeachae* SG2
46. *L. sainthelensi* SG2

Detection of amplified product:

The detection of the PCR products can be accomplished by direct visualization of the gels following ethidium bromide staining or by indirect means using specific nucleic acid hybridization probes. These methods are well known to those of skill and a general review of such techniques can be found in Nucleic Acid Hybridization, *A Practical Approach*, Eds. Hames and Higgins, IRL Press, Washington, D.C. 1985.

When detection of the PCR products is by hybridization as in a Southern blot, nucleic acid probes specifically complementary to a subsequence of the amplified region are used. Such probes are readily obtainable from the sequence of the amplified segment. Probes preferably hybridize to a DNA subsequence located between the primer binding subsequences to avoid any overlap of primer sequences and probe sequence. Preferred probes for the 5S rRNA and the mip gene of Legionella are provided in Table 2 (capture probes).

Depending on the assay format, it may be helpful to have labelled probes function to detect the amplified product. The probes can be labeled by any of the methods known in the art. Radioactive and enzyme labels are preferred. Most preferred are enzyme labels which in the presence of an appropriate substrate will produce a colored product. Examples include horseradish peroxidase and alkaline phosphatase. Color development can be accomplished by a variety of means using a variety of known substrates. Preferred methods for horseradish peroxidase include using tetramethylbenzidine (TMB) as described in *Clin. Chem.* 33(8):1368–1371 (1987). An alternative detection system is the Enhanced Chemiluminescent (ECL) detection kit commercially available from Amersham. The kit is used in accordance with the manufacturer's directions.

The electrophoresing conditions and the means for detecting the individual amplified oligonucleotides are well known and are not critical aspects of this invention. Any of the means accepted by those of skill will be applicable for this invention.

An alternative mode of detection of the amplified product is by sandwich hybridization onto membrane strips. In the typical arrangement, the strip is made of nylon and has oligonucleotide capture probes covalently bound in discrete spots.

To bind oligonucleotide capture probes to nylon, they are first tailed with oligothymidylic acid of about 100 bases. Tailing can be achieved using terminal transferase such as calf-thymus terminal deoxynucleotidyl transferase or polythymidine oligonucleotides can be chemically synthesized along with the probes. The tailed oligonucleotides are spotted onto the nylon strips. The strips are dried overnight and exposed to ultraviolet irradiation. The strips are then stored until hybridization assays are conducted. Additional details are provided in copending and co-assigned U.S. patent application, Ser. No. 347,495, filed May 4, 1989 is hereby incorporated by reference.

Capture probes are as described in tables 2 and 3 and are able to bind to the amplified products of the Legionella genome. Amplified product is allowed to bind to the membrane through hybridization to the capture probes. Amplified product is then detected by enzyme activity. A preferred means for detection of amplified product is to biotinylate each primer so that the amplified product is able to bind a streptavidin-horseradish peroxidase complex. The complex then permits detection of amplified product by chromagen development using commercially available substrates. Primer pairs may be biotinylated using the procedures described in Levenson C. and C. Chang, Nonisotypically Labeled Probes and Primers in *PCR Protocols,* Ed. Innis et al., Academic Press, Inc. 1990 at pages 99–112. Alternatively synthesis using a phosphoramidite linkage to directly biotinylate is available using reagents from Glenn Research.

Kits:

The primers of this invention can be embodied into kits for the detecting Legionella species in the environment. Such kits would include a variety of components. The kits would preferably include *Legionella pneumophila* DNA preferably a known pathogenic form such as the Bloomington isolate. This DNA will serve as a positive control. A bulk polymerase chain reaction mix which would contain optimized concentrations of Amplitaq® DNA Polymerase, a thermal resistant nucleic acid polymerase available from PECI, all 5S rRNA primers, all mip primers, dNTPs (dUTP preferably replacing dTTP), and buffer salts. An internal positive control sequence (IPC) is included to ensure that the PCR procedure functions properly. The IPC comprises an amplifiable target which acts as a positive control regardless of whether the Legionella target nucleic acid is present. In a preferred embodiment, the IPC comprises an unnatural sequence selected from a portion of the human HLA DQα gene. The gene sequences are flanked by sequences complementary to the upstream and downstream primers used to amplify subsequences of either the mip or 5 S RNA genes. Human HLA DQα is a sequence which is relatively rare in water samples and not likely to be present in the sample at a detectable level. The sequence for a preferred IPC is provided in Table 3. The IPC can be either double or single stranded and may be stored in the amplification reaction mixture or in a separate container. Typically, IPC is added to an amplification reaction mixture at 1 million to 10 million copies. For quantitation of Legionella present in the samples, one can use lower amounts of IPC, e.g., 100 to 100,000 copies. A 25 mM $MgCl_2$ solution is included to start the reaction by activation of Taq polymerase.

The kit may also comprise a means to detect the amplified product. Although any standard detection means can be used, such as a hybridization dot blot, agarose, or acrylamide gel electrophoresis, a preferred method uses a dip stick having a capture oligonucleotide which binds specifically to the amplified target. The dip stick captures the target and is detected by a non-isotopic detection system. For example the primers may be biotinylated before extension and a horseradish peroxidase/streptavidin complex used to bind the enzyme specifically to the capture site of the amplified target. A suitable substrate\buffer combination is 3, 3', 5, 5' tetra methylbenzidine (TMB) in 100 mM Sodium Citrate at pH 5.0.

Controlling visual density of nucleic acid hybridization assays:

In developing commercial quality kits, it is preferable to control the visual density of the detection system. Visual density conveys positive or negative results to the user and are important features of any commercial kit. It is the purpose of the present invention to provide a uniform and controllable visual density for such assays.

The basic problem arises from the desire to provide clear positive/negative signals when using stringent hybridization conditions. Nucleic acid hybridization assays attempting to distinguish between a defined group and less than all the group may benefit by placing in one site of a solid support, a mixture of the capture probes which individually could not capture all the different detection probes representing the group. Such assays will typically have a situs on a solid support bearing the mixture and other sites having less than all the different capture probes affixed thereto.

Without this invention, nucleic acid hybridization assays seeking to identify and distinguish between a group and less than all the group would not provide uniform density of detection when assaying samples containing similar concentrations of detection probes representing the entire group, a subgroup or different subgroups. The reason for the difference in visual density arises from the difference in the thermal melting temperatures [Tm] of the various nucleic acids comprising the assays. This problem becomes particularly acute in groups where the distinction between members can only be made by distinguishing between oligonucleotides having relatively few base differences, e.g. 1–5 base differences in a 30 base region. Such situations require stringent hybridization conditions and thus differences in thermal melting temperatures, not otherwise a problem, will lead to sharp distinctions between visual densities of positive results where equal concentrations of detection probes are present.

In brief this method provides for a method for controlling visual density of detection probes bound to capture probes in a nucleic acid hybridization assay. The assays typically have two or more different capture probes fixed to a solid support.

The capture probes are mixed in one site of the support according to an empirically determined proportion. A second site containing less than all the capture probes also prepared wherein the concentration of capture probe is approximately equal to the concentration of that probe present in the mixture. This proportion is designed to provide a uniform intensity of visual density between the two sites under a given hybridization condition and given detection probe concentration. The goal being to provide under stringent conditions a uniform density of label or uniform concentration of detection probes between the sites despite the differences in Tm between capture probes.

To assist in the understanding of this invention, a generic model is presented. The model is a nucleic acid hybridization assay kit for the detection of both pathogenic species in Genus A and for detection of the two species individually. The target nucleic acid will be a twenty base region of the 5S ribosomal RNA. This region will differ between the two species in that one species has a guanosine:cytosine instead of an adenosine:thymine pairing. Thus the Tm for species having the extra G:C pair is higher than for the other species.

The assay is as described herein for the Legionella assays. A collection of capture probes are first affixed to a solid support and PCR amplification product having biotin/streptavidin bound enzyme labels are used as detection probes. The array of capture probes on the solid support are three: (1) a first situs containing a mixture of 1:1 of the species specific capture probes to identify, none, either or both members of the genus; (2) a second situs containing only capture probes specific for species 1; and (3) a third situs containing only capture probes specific for species 2.

If the mixture of situs 1 is a 1:1 mixture, the density of the detection probes hybridized thereto for a given concentration of probes to in a test sample will provide density X+Y where X' and Y' are the relative proportion of detection probes specific to species 1 and 2 in a sample. The problem is that density X will not necessarily begin to equal Y where concentration of X' and Y' begin to equal each other in a sample. This is because under high stringent hybridization conditions, the numbers of detection probes in a aqueous sample that bind to capture probes will be different according to their respective thermal melting points.

One solution is to dilute the capture probe having the higher Tm to accommodate the capture probe having a lower Tm. For example in the above generic model, it is suggested that the mixture of capture probes to species 1 and 2 be diluted 1:1, 2:1, 1:2, 3:1 and 1:3. The other sites containing only one capture probe will be likewise diluted. A reference solution of detection probes at a given concentration is then used along with various dilutions to achieve a rough estimate of the visual density of the system for a given hybridization solution and detection/labelling system.

By further routine titration, it is possible to achieve a multiple dot nucleic acid hybridization system using highly stringent hybridization conditions where the visual density of the results from the detection system are equal for a given concentration of detection probe regardless of the Tms for the individual oligonucleotides. Such a system will have a mixture of capture probes in a given proportion affixed to a solid support and a concentration of individual capture probes affixed to another solid support or different region of the same solid support where the individual capture probes are present on the solid support in concentrations equivalent or approximately equivalent to their concentration in the mixture. It being further understood that the invention is equally applicable to situations where the mixture of probes are more complex than two members and the individual capture probes may represent multiple capture probes that are less than the entire group.

In the preferred assay format, the detection probe will be an amplification product wherein PCR is used to amplify a select target region of an organism. The PCR process yields biotinylated amplification products which serve as detection probes. These assays use a reference number of original copies in a given sample and the sensitivity of the assays is adjusted accordingly. For example, if a regulatory agency wants a detection level of 100 cells per liter and each cell has 10 copies of a target region, the assays can be designed to a collect one liter of sample and extract the nucleic acid from the collected cells. The 1000 targets are then amplified by 30 rounds of PCR at 95% efficiency to yield $5 \times 10^{11}$ copies. This number is then converted into moles using Avogadro number.

The sample of $5 \times 10^{11}$ copies represents the minimum acceptable sensitivity. The sample is then used as a reference against other cells in the group (at similar concentrations) to define conditions yielding an acceptable visual density for that concentration.

This process defines the dynamic range of an assay. The dynamic range are those concentrations of detection probes wherein the subsequent visual density is detectable and directly responsive to increases in the concentration of the detection probe. The dynamic range is defined empirically. It is simply a matter of routine titration to set out acceptable hybridization conditions and labelling systems to provide the desired dynamic range. For the colorimetric system described in this invention using TmB, the preferred dynamic range is between $10 \times 10^{-12}$ to about $100 \times 10^{-9}$ molar.

This invention has broad application to the field of nucleic acid hybridization. The means for affixing nucleic acids to solid supports, to detecting hybridized nucleic acid, to isolating, selecting and amplifying probes, and for formatting the assay including sandwich assays of three or more oligonucleotides and binary assays of two oligonucleotides are well known in the art. These features are not critical to the invention. For an overview of the underlying technology, see U.S. Pat. Nos. 5,015,569 and 4,886,741. A primer on this technology is *Nucleic Acid Hybridization, A Practical Approach*, Eds. Hames, B. D. and Higgins, S. J., ILR Press 1987. These three references are incorporated herein by reference.

An example of use of blended capture probes for development of a Legionella test kit is described in the Example section below. A target sequence of the 5S rRNA gene was used. The 5S RRNA nucleic acid sequence for organisms within the genus Legionella are quite similar to those of other genera (i.e., Pseudomonas and Vibrio). Within the genus Legionella the target nucleic acid sequence is not the same for all species. A blend of the two capture probes were made in order to detect most of the organisms of the genus Legionella in a single detection testing.

These two capture probes are 18 bases long and vary by one base; one probe has a "G" base where the other has a "A". The Tm of these two probes are approximately 60 and 58 C respectively. A titration was done to choose the proper ration of these capture probes and found to be in this case 1:1. A 1:1 mixture of the probes were made and the mixture was immobilized on a membrane. This mixture capture probe is used for the detection of the genus Legionella. This mixture makes it possible to detect most of the species of Legionella. If either of the probes were used alone only partial detection of the genus Legionella would be possible under stringent conditions. Under reduced stringent conditions, non-Legionella organisms with similar 5S rRNA sequences such as organisms of the genus Pseudomonas could also be detected and produce false positive results.

It will be apparent to those of skill that various substitutions and modifications may be made to the invention disclosed herein without departing from the scope and spirit of the invention. The following examples are provided for illustration purposes and should not be construed as a limitation of this invention.

EXAMPLES

A. Isolation of Sample DNA

A water sample of between 100 to 500 ml is first filtered through a 25 mm, 0.45µ pore filter (Durapore from Millipore). The filter is transferred to a tube containing 2 ml of DNA extraction reagent (20% Chelex resin, 10 mM Tris-HCl, 0.1 mM EDTA pH 8.0) and vortexed to free the organisms from the filter surface. The sample is placed in a boiling water bath and heated to 99° C. in a heat block for 10 min to lyse the organisms.

B. PCR Amplification of the Leqionella genome

As previously stated, the preferred PCR procedure is a multiplex reaction where both the mip and 5S rRNA target regions are amplified simultaneously in the PCR mixture. A 20 µl sample from the above test solution is removed and added to 65 µl of an amplification reaction mix containing the following: PCR buffer (50 mM KCl, 50 mM Tris-HCl at pH 8.9); 4 units of Taq DNA polymerase (from PECI), 0.35 mM dNTPs and 0.5 µM of each primer. The primers are described in table 2. Three hundred copies of the internal positive control (IPC) sequence is added to the reaction mixture. The IPC sequence is provided in Table 3. The sequences extending beyond PT70 are not amplified and can be deleted.

The target 5S rRNA gene subsequence of the Legionella genus and the target subsequence of the mip gene of *Legionella pneumophila* are amplified using PCR procedures which follow.

TABLE 2

Primers and Probes for Amplifying and Detecting Legionella species.*

Left mip primer: PT69: GCATTGGTGCCGATTTGG; Seq. ID No. 6
Right mip primer: PT70: GCTTTGCCATCAAATCTTTCTGAA; Seq. ID No. 7
Right mip primer: PT181: GTTTTGCCATCAAATCTTTTTGAA; Seq. ID No. 23
Left 5S rRNA primer: PT82: GGCGACTATAGCGRTTTGGAA; Seq. ID No. 10
Left 5S rRNA primer: PT159: GGCGACTATAGCGGTGTGGAA; Seq. ID No. 21
Right 5S rRNA primer: PT80: GCGATGACCTACTTTCRCATGA; Seq. ID No. 9
Right 5S rRNA primer: PT157: GCGATGACCTACTTTCGCATG; Seq. ID No. 22
mip capture probe: PT56: TTGCTTCCGGATTAACATCT; Seq. ID No. 4
mip capture probe: PT35: CAAGGCATAGATGTTAATCCGG; Seq. ID No. 2
mip capture probe: PT55: CATAGCGTCTTGCATGCCTTTAGCC; Seq. ID No. 3**
mip capture probe: PT67: AACCGAACAGCAAATGAAAGACG; Seq. ID No. 5
5S rRNA capture probe: PT77: CGCGCCAATGATAGTGTGA; Seq. ID No. 8
5S rRNA capture probe: PT100: CATCTCGAACTCAGAAGTGAAAC; Seq. ID No. 11
5S rRNA capture probe: PT125: GCGCCAATGATAGTGTG; Seq. ID No. 24
5S rRNA capture probe: PT127: GCGCCGATGATAGTGTG; Seq. ID No. 25

*Unless stated otherwise all sequences are presented 5' to 3'.
**preferred sequences The solution is overlayed with 75 µl of light mineral oil (Sigma Chemical Co., St. Louis, Mo.), 15 µl of 25 mM MgCl$_2$ is added and the solution is subjected to the following thermal profile using a 1 second setting to change temperatures as rapidly as possible using the Perkin-Elmer Cetus DNA Thermocycler:

1 second to 95° C.

95° C. for 1 Min.

30 cycles of:

1 second to 95° C.

95° C. for 1 Min.

1 second to 63° C.

63° C. for 1.5 Min. followed by 72° C. for 7 min and shutdown or hold at 6° C.

TABLE 3

Internal Positive Control Sequence (IPC) PT74 and Capture Probes.

Seq. ID No. 1

5'-G C A T T G G T G C C G A T T T G G G G A A G T T T G A T G G A G A T G A G G A G T T C T A C G
 * * * * P T 6 9 * * * * * * * * * *
                                                    ... 1.2, 1.3, 4 ......>

T G G A C C T G G A G A G G A A G G A G A C T G C C T G G C G G T G G C C T G A G T T C A G C A
. .
                                                                        ... 1 probe A A T T T G G A G G T T T T G T T C A G A A A G A T T T G A T G G C A A A G C G T A C T G C T G A A T T C A-3'
. . . . . . . . . .
                        3'  * * * * * P T 7 0 * * * * * * * * * * * * * *   5'

Positive Control - DQα1

5'- T G A G T T C A G C A A A T T T G G A G -3';  Seq. ID No. 16

Negative Control - DQα 1.2, 1.3, 4
                                *
    5'- G A T G A G C A G T T C T A C G T G G-3'; Seq. ID No. 17

*represents a single mismatched base pair.

C. Detection of Amplified DNA

Ten microliters of the PCR reaction mixture and 2 µl of a loading gel are mixed and applied to each lane of a 3.0% Nusieve® and 1% Seakem® brand agarose gel (FMC Corp., Rockland, Me.) using TBE electrophoresis buffer (89 mM, Tris HCl, 89 mM, sodium borate and 1 mM EDTA at pH 8.2. The loading buffer is 250 mg/ml Ficol 400, 0.25 mg/ml Bromophenol Blue. The gel is 20 cm long and 12.5 cm wide. It is run horizontally for approximately 2 hours at 150 volts. The contents of the gel are then viewed under UV light after ethidium bromide staining.

The sensitivity of this assay permits the detection of 100 copies of the target regions per 10 μl sample. Using primers PT69, PT70 and PT181, the amplified mip region is approximately 168 bp and the amplified 5S rRNA region is approximately 107 bp. Under the above conditions the amount of amplified products are approximately equal.

Alternatively the amplified products can be captured on a nylon membrane using capture probes as illustrated in tables 2 and 3. A mixture of probes PT125 and PT127 gives superior hybridization results when testing for unknown strains of Legionella. The probes are bound to a Pall Biodyne-B nylon membrane (Pall Biosupport Div., East Hills, N.Y.).

In a preferred embodiment mixtures represented by PT82 and PT80 are amplified. Eliminating PT 159 and 157 decreases slightly the specificity of the assay for *L. spiritensis, sainthelensi* (SG1 and SG2), and *quinlivanii*. However the assay is now substantially decreases the undesired amplification of rRNA from Pseudomonas sps. More specifically the nonspecific crossreaction is reduced so that 100 copies of a Legionella specific target nucleic acid will equal $10^5$ to $10^7$ cross-reacting Pseudomonas specific target.

The capture probes are optionally combined with p-[2-hydroxy-1-naphthyl azo]-benzenesulfonic acid, Orange-11 dye (certified), from Sigma chemical Co., St. Louis, Mo. The dye is diluted to 0.01% in 50 mM 3-[cyclohexylamino]-1-propanesulfonic acid (CAPS) adjusted to pH 10.0 using sodium hydroxide.

Nylon membrane is cut into strips having a combination of capture probes PT125 and PT127 for 5S RNA, PT55 for the mip gene and the positive and negative control probes depicted in table 3. Approximately 4 picomoles of each probe are bound to the membrane in discrete spots. The membrane is then washed with a mixture of 0.5% SDS w/v, 5× SSPE (diluted from 20× standard saline phosphate EDTA buffer pH 7.4 as prepared in Sambrook, Molecular Cloning A Laboratory Manual, Cold Spring Harbor Laboratory Press, 1989) and 0.03% dextran sulfate.

Forty μl of denaturation solution (1.2N NaOH, 0.11M EDTA) is added to the exemplified sample. A 50 μl sample of the denatured sample is added to approximately 3 milliliters of hybridization solution comprising 0.5% w/v SDS in 5× SSPE. The nylon membranes with capture probes bound thereto are each exposed to 3 ml of hybridization solution in a water bath under gentle rotation at 50°–55° C. for 20 min.

The hybridization solution is decanted from the membranes and biotinylated amplified target bound to the membrane is linked to horseradish peroxidase through streptavidin. The enzyme is attached by incubating the membranes under gentle rotation in a 50°–55° C. water bath for 20 minutes in 3.0 ml of 2.5× SSPE with 0.10% w/v SDS and 25 μl of a commercially available streptavidin-horseradish peroxidase solution (AmpliType Kit™ DQα DNA typing kit from Perkin Elmer Cetus). The nylon membrane are washed once for 12 minutes at 50°–55° C. under gentle rotation in an excess of 2.5× SSPE with 0.1% w/v SDS as wash buffer and finally washed with shaking at room temperature for 5 minutes in 2.5× SSPE with 0.1% SDS and again in 0.1M sodium citrate at pH 5.0.

Color development is achieved by using 3,3',5,5' tetramethylbenzidine (TmB). 0.25 ml of a TMB stock solution of 2 mg/ml in ethanol is diluted in 5 ml of 0.5M sodium citrate at pH 5.0 and 1 μl of a standard solution of hydrogen peroxide. The membranes are incubated at room temperature for 30 minutes in the presence of this solution in the dark. The membranes are then rinsed twice in 10 ml of water at room temperature and results are recorded.

---

What is claimed is:

1. A process for amplifying a nucleic acid sequence from Legionella species, comprising carrying out a polymerase chain reaction using primers selected from the group consisting of 5'-GCATTGGTGCCGATTTGG-3', Seq. ID No. 6;
5'-GCTTTGCCATCAAATCTTTCTGAA-3', Seq. ID No. 7;
5'-GGCGACTATAGCGRTTTGGAA-3', Seq. ID No. 10;
5'-GCGATGACCTACTTTCRCATGA-3', Seq ID No. 9; and
5'-GTTTTGCCATCAAATCTTTTTGAA-3', Seq. ID No. 23;

where R represents an adenine or a guanine base and the primers having a base R are a mixture of the two primers.

2. The process of claim 1, wherein said polymerase chain reaction is carried out using primers 5'-GCATTGGTGCCGATTTGG-3', Seq. ID No. 6;
5'-GCTTTGCCATCAAATCTTTCTGAA-3', Seq. ID No. 7;
5'-GGCGACTATAGCGRTTTGGAA-3', Seq. ID No. 10;
5'-GCGATGACCTACTTTCRCATGA-3', SEQ ID No. 9; and
5'-GTTTTGCCATCAAATCTTTTTGAA-3', Seq. ID No. 23.

3. The process of claim 1 which further comprises co-amplifying with said nucleic acid sequence from Legionella species, an internal positive control oligonucleotide comprising a non-Legionella nucleotide sequence and a Legionella nucleotide sequence, wherein said Legionella nucleotide sequence is selected from the group consisting of 3'-CGTAACCACGGCTAAACC-5', Seq. ID No. 12;
3'-CGAAACGGTAGTTTAGAAAGACTT-5', Seq. ID No. 13;
3'-CCGCTGATATCGCYAAACCTT-5', Seq. ID No. 14;
3'-CGCTACTGGATGAAAGYGTACT-5', Seq. ID No. 15;
3'-CAAAACGGTAGTTTAGAAAAACTT-5', Seq. ID No. 20;

where Y represents a cytosine or thymine base, and wherein said Legionella nucleotide sequence is upstream of said non-Legionella nucleotide sequence.

4. A process for detecting a nucleic acid sequence from Legionella species, comprising:

(a) carrying out a polymerase chain reaction using primers selected from the group consisting of
5'-GCATTGGTGCCGATTTGG-3', Seq. ID No. 6;
5'-GCTTTGCCATCAAATCTTTCTGAA-3', Seq. ID No. 7;
5'-GGCGACTATAGCGRTTTGGAA-3', Seq. ID No. 10;
5'-GCGATGACCTACTTTCRCATGA-3', SEQ ID No. 9; and
5'-GTTTTGCCATCAAATCTTTTTGAA-3', Seq. ID No. 23;

where R represents an adenine or a guanine base and the primers having a base R are a mixture of the two primers; and (b) hybridizing the amplification product of step (a) with a probe selected from the group consisting of
3'-CCGCTGATATCGCCACACCTT-5', Seq. ID No. 18;
3'-CGCTACTGGATGAAAGCGTAC-5', Seq. ID No. 19; and
3'-CAAAACGGTAGTTTAGAAAAACTT-5', Seq. ID No. 20.

5. The process of claim 4, wherein said polymerase chain reaction is carried out using primers 5'-GCATTGGTGCCGATTTGG-3', Seq. ID No. 6;
5'-GCTTTGCCATCAAATCTTTCTGAA-3', Seq. ID No. 7;

5'-GGCGACTATAGCGRTTTGGAA-3', Seq. ID No. 10;
5'-GCGATGACCTACTTTCRCATGA-3', SEQ ID No. 9; and
5'-GTTTTGCCATCAAATCTTTTTGAA-3', Seq. ID No. 23;

and wherein said hybridization is carried out using probes

3'-CCGCTGATATCGCCACACCTT-5', Seq. ID No. 18;
3'-CGCTACTGGATGAAAGCGTAC-5', Seq. ID No. 19; and
3'-CAAAACGGTAGTTTAGAAAAACTT-5', Seq. ID No. 20.

6. The process of claim 4 which further comprises co-amplifying with said nucleic acid sequence from Legionella species, an internal positive control oligonucleotide sequence comprising a non-Legionella nucleotide sequence and a Legionella nucleotide sequence, wherein said Legionella nucleotide sequence is selected from the group consisting of 3'-CGTAACCACGGCTAAACC-5', Seq. ID No. 12;
3'-CGAAACGGTAGTTTAGAAAGACTT-5', Seq. ID No. 13;
3'-CCGCTGATATCGCYAAACCTT-5', Seq. ID No. 14;
3'-CGCTACTGGATGAAAGYGTACT-5', Seq. ID No. 15;
3'-CAAAACGGTAGTTTAGAAAAACTT-5', Seq. ID No. 20;

where Y represents a cytosine or thymine base, and wherein said Legionella nucleotide sequence is upstream of said non-Legionella nucleotide sequence.

* * * * *

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
( A ) LENGTH: 150 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

```
GCATTGGTGC CGATTTGGGG AAGTTTGATG GAGATGAGGA GTTCTACGTG GACCTGGAGA      60

GGAAGGAGAC TGCCTGGCGG TGGCCTGAGT TCAGCAAATT TGGAGGTTTT GTTCAGAAAG     120

ATTTGATGGC AAAGCGTACT GCTGAATTCA                                      150
```

( 2 ) INFORMATION FOR SEQ ID NO:2:

( i ) SEQUENCE CHARACTERISTICS:
( A ) LENGTH: 22 base pairs
( B ) TYPE: nucleic acid (C) STRANDEDNESS: single
(D) TOPOLOGY: linear (ii) MOLECULE TYPE: DNA (probe)

(xi) SEQUENCE DESCRIPTION: SEQ ID NO:2:

CAAGGCATAG ATGTTAATCC GG 22

(2) INFORMATION FOR SEQ ID NO:3:

(i) SEQUENCE CHARACTERISTICS:
 (A) LENGTH: 25 base pairs
 (B) TYPE: nucleic acid
 (C) STRANDEDNESS: single
 (D) TOPOLOGY: linear (ii) MOLECULE TYPE: DNA (probe)

(xi) SEQUENCE DESCRIPTION: SEQ ID NO:3:

CATAGCGTCT TGCATGCCTT TAGCC 25

(2) INFORMATION FOR SEQ ID NO:4:

(i) SEQUENCE CHARACTERISTICS:
 (A) LENGTH: 20 base pairs
 (B) TYPE: nucleic acid
 (C) STRANDEDNESS: single
 (D) TOPOLOGY: linear (ii) MOLECULE TYPE: DNA (probe)

(xi) SEQUENCE DESCRIPTION: SEQ ID NO:4:

TTGCTTCCGG ATTAACATCT 20

(2) INFORMATION FOR SEQ ID NO:5:

(i) SEQUENCE CHARACTERISTICS:
 (A) LENGTH: 23 base pairs
 (B) TYPE: nucleic acid
 (C) STRANDEDNESS: single
 (D) TOPOLOGY: linear (ii) MOLECULE TYPE: DNA (probe)

(xi) SEQUENCE DESCRIPTION: SEQ ID NO:5:

AACCGAACAG CAAATGAAAG ACG 23

(2) INFORMATION FOR SEQ ID NO:6:

(i) SEQUENCE CHARACTERISTICS:
 (A) LENGTH: 18 base pairs
 (B) TYPE: nucleic acid
 (C) STRANDEDNESS: single
 (D) TOPOLOGY: linear (ii) MOLECULE TYPE: DNA (primer)

(xi) SEQUENCE DESCRIPTION: SEQ ID NO:6:

GCATTGGTGC CGATTTGG 18

(2) INFORMATION FOR SEQ ID NO:7:

(i) SEQUENCE CHARACTERISTICS:
 (A) LENGTH: 24 base pairs
 (B) TYPE: nucleic acid
 (C) STRANDEDNESS: single
 (D) TOPOLOGY: linear (ii) MOLECULE TYPE: DNA (primer)

( x i ) SEQUENCE DESCRIPTION: SEQ ID NO:7:

GCTTTGCCAT CAAATCTTTC TGAA                                                      24

( 2 ) INFORMATION FOR SEQ ID NO:8:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:8:

CGCGCCAATG ATAGTGTGA                                                            19

( 2 ) INFORMATION FOR SEQ ID NO:9:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:9:

GCGATGACCT ACTTTCRCAT GA                                                        22

( 2 ) INFORMATION FOR SEQ ID NO:10:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:10:

GGCGACTATA GCGRTTTGGA A                                                         21

( 2 ) INFORMATION FOR SEQ ID NO:11:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:11:

CATCTCGAAC TCAGAAGTGA AAC                                                       23

( 2 ) INFORMATION FOR SEQ ID NO:12:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:12:

CCAAATCGGC ACCAATGC                                                             18

( 2 ) INFORMATION FOR SEQ ID NO:13:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:13:

TTCAGAAAGA TTTGATGGCA AAGC      24

( 2 ) INFORMATION FOR SEQ ID NO:14:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:14:

TTCCAAA Y CG CTATAGTCGC C      21

( 2 ) INFORMATION FOR SEQ ID NO:15:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (primer)

( x i ) SEQUENCE DESCRIPTION: SEQ ID NO:15:

TCATG Y GAAA GTAGGTCATC GC      22

( 2 ) INFORMATION FOR SEQ ID NO:16:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:16:

TGAGTTCAGC AAATTTGGAG      20

( 2 ) INFORMATION FOR SEQ ID NO:17:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:17:

GATGAGCAGT TCTACGTGG      19

( 2 ) INFORMATION FOR SEQ ID NO:18:

( i ) SEQUENCE CHARACTERISTICS:
        ( A ) LENGTH: 21 base pairs
        ( B ) TYPE: nucleic acid (C) STRANDEDNESS: single
(D) TOPOLOGY: linear (ii) MOLECULE TYPE: DNA (primer)

(xi) SEQUENCE DESCRIPTION: SEQ ID NO:18:

TTCCACACCG CTATAGTCGC C                                                                                          21

(2) INFORMATION FOR SEQ ID NO:19:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: DNA (primer)

(xi) SEQUENCE DESCRIPTION: SEQ ID NO:19:

CATGCGAAAG TAGGTCATCG C                                                                                          21

(2) INFORMATION FOR SEQ ID NO:20:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: DNA (primer)

(xi) SEQUENCE DESCRIPTION: SEQ ID NO:20:

TTCAAAAAGA TTTGATGGCA AAAC                                                                                       24

(2) INFORMATION FOR SEQ ID NO:21:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: DNA (primer)

(xi) SEQUENCE DESCRIPTION: SEQ ID NO:21:

GGCGACTATA GCGGTGTGGA A                                                                                          21

(2) INFORMATION FOR SEQ ID NO:22:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: DNA (primer)

(xi) SEQUENCE DESCRIPTION: SEQ ID NO:22:

GCGATGACCT ACTTTCGCAT G                                                                                          21

(2) INFORMATION FOR SEQ ID NO:23:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (ii) MOLECULE TYPE: DNA (primer)

( x i ) SEQUENCE DESCRIPTION: SEQ ID NO:23:

GTTTTGCCAT CAAATCTTTT TGAA 24

( 2 ) INFORMATION FOR SEQ ID NO:24:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:24:

GCGCCAATGA TAGTGTG 17

( 2 ) INFORMATION FOR SEQ ID NO:25:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (probe)

( x i ) SEQUENCE DESCRIPTION: SEQ ID NO:25:

GCGCCGATGA TAGTGTG 17